(12) United States Patent
Coates et al.

(10) Patent No.: US 6,414,092 B1
(45) Date of Patent: *Jul. 2, 2002

(54) CHOLESTERIC FLAKES

(75) Inventors: David Coates, Wimborne; Mark Goulding, Poole; Alison May, Wimborne, all of (GB)

(73) Assignee: Merck Patent Gesellschaft mit beschraenkter Haftung (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/722,670

(22) Filed: Nov. 28, 2000

Related U.S. Application Data

(62) Division of application No. 09/125,295, filed as application No. PCT/EP97/00433 on Feb. 1, 1997, now Pat. No. 6,207,770.

(30) Foreign Application Priority Data

Feb. 15, 1996 (EP) .............................. 96102263

(51) Int. Cl.$^7$ ................................. C08G 85/00
(52) U.S. Cl. ................... 526/63; 106/493; 252/299.01
(58) Field of Search ........................................... 526/63

(56) References Cited

U.S. PATENT DOCUMENTS

| | | | | |
|---|---|---|---|---|
| 5,362,315 A | * | 11/1994 | Mueller-Rees et al. | ..... 106/493 |
| 5,364,557 A | * | 11/1994 | Faris | ..... 252/299.01 |
| 5,560,864 A | | 10/1996 | Goulding | |
| 5,599,412 A | * | 2/1997 | Faris | ..... 156/73.3 |
| 5,807,497 A | | 9/1998 | Gailberger et al. | |
| 5,942,030 A | | 8/1999 | Schulmacher et al. | |

FOREIGN PATENT DOCUMENTS

| CA | 2190879 | 11/1995 |
|---|---|---|
| CA | 2148765 | 12/1995 |
| DE | 19504224 | 8/1995 |
| DE | 4418076 | 11/1995 |
| EP | 685749 | 12/1995 |
| EP | 724005 | 7/1996 |
| GB | 2276883 | 10/1994 |
| GB | 2297556 | 8/1996 |
| GB | 2298202 | 8/1996 |

\* cited by examiner

Primary Examiner—Paul R. Michl
(74) Attorney, Agent, or Firm—Millen, White, Zelano & Branigan, P.C.

(57) ABSTRACT

The invention relates to cholesteric polymer flakes obtainable from a chiral polymerizable mesogenic material, to methods of manufacturing such cholesteric flakes, to the use of certain chiral and achiral polymerizable compounds with one or more terminal polymerizable groups for the manufacturing of such flakes and to the use of such cholesteric flakes as effect pigments in spraying or printing inks or paints or colored plastics for different applications, especially for automotive use, cosmetic products and security applications.

35 Claims, No Drawings

CHOLESTERIC FLAKES

This is a division, of application Ser. No. 09/125,295 filed Aug. 14, 1998 now U.S. Pat. No. 6,207,770 which is a 371 of PCT/EP97/00433, filed Feb. 9, 1997.

FIELD OF THE INVENTION

The invention relates to cholesteric polymer flakes obtainable from a chiral polymerizable mesogenic material. The invention also relates to methods of manufacturing such cholesteric flakes.

The invention further relates to the use of certain chiral and achiral polymerizable compounds with one or more terminal polymerizable groups for the manufacturing of such flakes.

The invention also relates to the use of such cholesteric flakes as effect pigments in spraying or printing inks or paints or colored plastics for different applications, especially for automotive use, cosmetic products and security applications.

BACKGROUND OF THE INVENTION

Cholesteric liquid crystals exhibit a helically twisted molecular orientation resulting in special optical properties. When a cholesteric LC is irradiated with unpolarized light, interaction of the helix structure with incident light of a selected wavelength will result in reflection of 50% of its intensity as circularly polarized light of a given handedness (left-handed or right-handed according to the handedness of the helix) while the other 50% are transmitted as circularly polarized light of the opposite handedness. The wavelength λ of the reflection maximum depends on the pitch p of the helix and the average refractive index n of the cholesteric LC material according to the following formula:

$$\lambda = n \cdot p$$

Since the color effect of cholesteric optical materials is based on selective light reflection and not on absorption like in conventional dyes or pigments, extraordinary color properties can be obtained like for example higher color saturation, wider color range and iridescent appearance. These materials exhibit a unique reflection pattern, because the reflected wavelength will change if the incident light propagates through the cholesteric LC at an angle to the direction of the helix axis.

However, to achieve good color properties when applied in inks or paints, a uniform alignment of the cholesteric LC with the orientation of the helix axis parallel to the viewing direction is required. Furthermore, low molar mass cholesteric LC's are best used in most applications in the liquid state if they are confined to small capsules or droplets. In this case the temperature dependence of the reflected wavelength is another problem. On the other hand polymeric cholesteric LC's which are used in the solid state have to be aligned above their glass transition or melting temperature respectively which requires high temperatures. Both embodiments are therefore inconvenient for production and limited in their applications.

By making flakes or platelets of prealigned cholesteric polymer material several problems of the prior art can be circumvented. To produce such flakes a cholesteric polymer material is coated onto a substrate and aligned to achieve uniform orientation of the helical axis normal to the surface. The film is then cured and ground to yield small flat flakes which can be dispersed e.g. in a transparent binder for the use as inks or paints. These inks can be used at room temperature without the need of further alignment.

PRIOR ART

Such polymer flakes have been described earlier. In U.S. Pat. No. 5,364,557 flakes based on cholesteric LC polysiloxanes are disclosed. However, the alignment of an LC polymer as described there is difficult to achieve and has to be carried out above the glass transition, which requires high temperatures (120 to 150° C.) and optionally auxiliary alignment means such as electric or magnetic fields.

Patent Application WO 94/22976 describes flakes made by coating two separate films of cholesteric LC polysiloxanes which are aligned at high temperatures, optionally crosslinked and subsequently laminated together or are coated on different sides of a base polymer plate. As an alternative low molar mass cholesteric LC's with high melting points are described which have to be cooled down rapidly after alignment to obtain an oriented glass. However, these methods require high temperature changes and, as the application is confined to laminae of cholesteric materials, imply a complicated production process with many subsequent steps.

Furthermore, both documents describe the preferred use of prefabricated cholesteric LC side chain polysiloxanes. As it is known to the skilled in the art such polymers are usually synthesized by attaching mesogenic side chains in a polymer analogous addition reaction to a polysiloxane backbone which has been polymerized in advance. Since the optical properties and thus the color appearance of the polymer flakes are depending mainly on the ratio and the chemical structure of the mesogenic side chains, they are already determined in the polymer prior to the flake preparation. On the other hand the mechanical properties of the flakes are heavily influenced by the chain length and the crosslink density of the polymer, which are fixed during synthesis of the polysiloxane backbone and/or during flake production. It is therefore difficult to control all physical and material properties of the pigment flakes obtained in this way.

The German Application DE 4,419,239 describes cholesteric pigment flakes made of three dimensional chiral polymer networks and containing polysiloxanes with cholesterol side chains and methacrylate groups as crosslinking agent. However, besides cholesterol no other chiral groups are disclosed. Furthermore, the polymer material also has to be prepared in two subsequent polymerization steps as described above.

SUMMARY OF THE INVENTION

Thus the aim of this invention is to provide cholesteric flakes for use as pigments that can be made in a very simple manner which also enables easy and direct control of the optical and mechanical properties of the product.

It was now found that this can be achieved by using certain polymerizable mesogenic materials and a process according to the present invention.

The term "flakes" as it is used throughout the claims and the description of this invention comprises small size particles with dimensions of 1 μm to 2 mm. For example, these particles can be granules of a symmetric or unsymmetric shape, or platelets having average lateral dimensions several times larger than the thickness, or mixtures of both platelets and granules.

One of the objects of the invention are cholesteric flakes obtainable from a chiral polymerizable mesogenic material by a process including the following steps:

(a) coating said material onto a substrate which is then optionally covered by a second substrate,
(b) aligning the coated material into a planar orientation,
(c) curing the aligned material into a polymer film,
(d) removing the polymer film from the substrate, and
(e) grinding it, optionally under cooling.

In a preferred embodiment of the present invention the chiral polymerizable mesogenic material comprises at least two polymerizable mesogenic compounds exhibiting at least one terminal poymerizable group that is linked, optionally via a spacer group, to a mesogenic core and is selected from the following formulae:

$$CH_2=CW-COO- \qquad I1$$
$$WCH=CH-O- \qquad I2$$
$$CH_2=CH-Ph-(O)_n- \qquad I3$$

   I4 in which W denotes H, $CH_3$ or Cl and n is 0 or 1.

In another preferred embodiment of the invention the chiral polymerizable mesogenic material comprises at least two polymerizable mesogenic compounds, wherein each of said compounds exhibits a polymerizable group of the formulae |1 to |4 that is different from at least one other compound.

In another preferred embodiment of the present invention the chiral polymerizable mesogenic material is comprising at least one achiral polymerizable mesogenic compound and at least one chiral polymerizable mesogenic compound, wherein at least one of these compounds exhibits two or more polymerizable groups.

In another preferred embodiment of the invention at least one of the polymerizable mesogenic compounds is a fumarate.

In another preferred embodiment the achiral polymerizable mesogenic compound exhibits two or more polymerizable groups.

In another preferred embodiment the chiral polymerizable mesogenic compound exhibits two or more polymerizable groups.

In another preferred embodiment the chiral polymerizable mesogenic material comprises at least one photoinitiator.

In another preferred embodiment the chiral polymerizable mesogenic material comprises a non mesogenic compound with one or more polymerizable groups.

In another preferred embodiment the substrate in step (a) is a polyester film.

Yet in another preferred embodiment the film obtained in step (c) has a thickness of 4–10 μm.

Another object of the invention is the use of cholesteric flakes as described above as effect pigments for printing inks, spray paints, automotive use, cosmetic products or colored plastics.

Yet another object of the invention is the use of cholesteric flakes as described above for active and passive optical elements or as pigments in inks and paints for security applications.

Other aims of the present invention are immediately evident to the person skilled in the art from the following detailed description.

DETAILED DESCRIPTION OF THE INVENTION

The achiral and chiral polymerizable mesogenic compounds are preferably selected according to the following formula II:

$$P-(Sp)_n-MG-R \qquad II$$

wherein
P is a polymerizable group selected of formulae I1 to I4,
Sp is a spacer group having 1 to 20 C atoms,
R is H, halogen or cyano or a chiral or achiral organic group that may be linear or branched or, in compounds exhibiting more than one polymerizable group, has the meaning given for $P-(Sp)_n-$,
n is 0 or 1, and
MG is a mesogenic or mesogenity supporting group, preferably linked to the spacer group Sp and the organic group R by an ester or ether group or a single bond.

In the compounds of formula II P is preferably a vinyl group, an acrylate or methacrylate group, a styrene group or an epoxy group. Especially preferably P is an acrylate or methacrylate group.

Particularly preferred compounds of formula II are those wherein
MG is a mesogenic or mesogenity supporting group, preferably selected according to formula III $$-(A^1-Z^1)_m-A^2-Z^2-A^3- \qquad III$$

wherein
$A^1$, $A^2$ and $A^3$ are independently from each other 1,4-phenylene in which, in addition, one or more CH groups may be replaced by N, 1,4-cyclohexylene in which, in addition, one or two non-adjacent $CH_2$ groups may be replaced by O and/or S, 1,4-cyclohexenylene or naphthalene-2,6-diyl, it being possible for all these groups to be unsubstituted, mono- or polysubstituted with halogen, cyano or nitro groups or alkyl, alkoxy or alkanoyl groups having 1 to 7 C atoms wherein one or more H atoms may be substituted by F or Cl,
$Z^1$ and $Z^2$ are each independently $-COO-$, $-OCO-$, $-CH_2CH_2-$, $-OCH_2-$, $-CH_2O-$, $-CH=CH-$, $-C\equiv C-$, $-CH=CH-COO-$, $-OCO-CH=CH-$ or a single bond and
m is 0, 1 or 2,
and
R is an alkyl radical with up to 25 C atoms which may be unsubstituted, mono- or polysubstituted by halogen or CN, it being also possible for one or more non-adjacent $CH_2$ groups to be replaced, in each case independently from one another, by $-O-$, $-S-$, $-NH-$, $-N(CH_3)-$, $-CO-$, $-COO-OCO-$, $-OCO-O-$, $-S-CO-$, $-CO-S-$ or $-C\equiv C-$ in such a manner that oxygen atoms are not linked directly to one another, or alternatively R is halogen, cyano or has independently one of the meanings given for $P-(Sp)_n-$.

Particularly preferred is a chiral polymerizable mesogenic material comprising at least two polymerizable mesogenic compounds at least one of which is a compound of formula II.

In another preferred embodiment of the invention the polymerizable mesogenic compounds are selected according to formula II, wherein R has one of the meanings of $P-(Sp)_n-$ as given above.

Bicyclic and tricyclic mesogenic compounds are preferred.

Of the compounds of formula II especially preferred are those in which R is F, Cl, cyano, or optionally halogenated alkyl or alkoxy, or has the meaning given for P—(Sp)$_n$—, and MG is of formula III wherein Z$^1$ and Z$^2$ are —COO—, —OCO—, —CH$_2$—CH$_2$—, —CH=CH—COO—, —OCO— CH=CH— or a single bond.

A smaller group of preferred mesogenic groups of formula III is listed below. For reasons of simplicity, Phe in these groups is 1,4-phenylene, Phe L is a 1,4-phenylene group which is substituted by at least one group L, with L being F, Cl, CN or an optionally fluorinated alkyl, alkoxy or alkanoyl group with 1 to 4 C atoms, and Cyc is 1,4-cyclohexylene.

| | |
|---|---|
| —Phe-Z$^2$-Phe— | III-1 |
| —Phe-Z$^2$-Cyc— | III-2 |
| —PheL-Z$^2$-Phe— | III-3 |
| —PheL-Z$^2$-Cyc— | III-4 |
| —Phe-Z$^2$-PheL— | III-5 |
| —Phe-Z$^1$-Phe-Z$^2$-Phe— | III-6 |
| —Phe-Z$^1$-Phe-Z$^2$-CyC— | III-7 |
| —Phe-Z$^1$-Cyc-Z$^2$-Phe— | III-8 |
| —Phe-Z$^1$-Cyc-Z$^2$-Cyc— | III-9 |
| —Phe-Z$^1$-PheL-Z$^2$-Phe— | III-10 |
| —Phe-Z$^1$-Phe-Z$^2$-PheL— | III-11 |
| —PheL-Z$^1$-Phe-Z$^2$-PheL— | III-12 |
| —PheL-Z$^1$-PheL-Z$^2$-Phe— | III-13 |
| —PheL-Z$^1$-PheL-Z$^2$-PheL— | III-14 |

In these preferred groups Z$^1$ and Z$^2$ have the meaning given in formula I described above. Preferably Z$^1$ and Z$^2$ are —COO—, —OCO—, —CH$_2$CH$_2$—, —CH=CH—COO— or a single bond.

L is preferably F, Cl, CN, NO$_2$, CH$_3$, C$_2$H$_5$, OCH$_3$, OC$_2$H$_5$, COCH$_3$, COC$_2$H$_5$, CF$_3$, OCF$_3$, OCHF$_2$, OC$_2$F$_5$, in particular F, Cl, CN, CH$_3$, C$_2$H$_5$, OCH$_3$, COCH$_3$ and OCF$_3$, most preferably F, CH$_3$, OCH$_3$ and COCH$_3$.

Particularly preferred are compounds wherein MG is selected from the following formulae

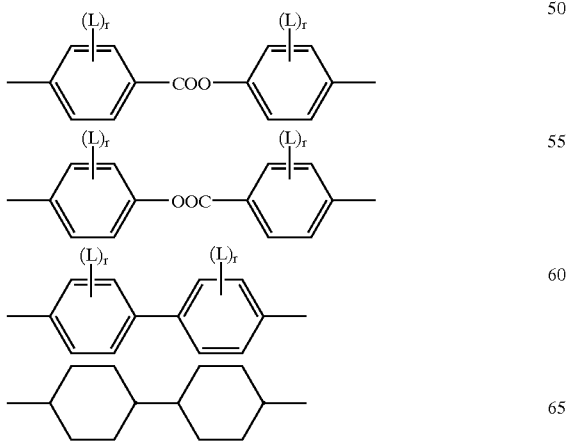
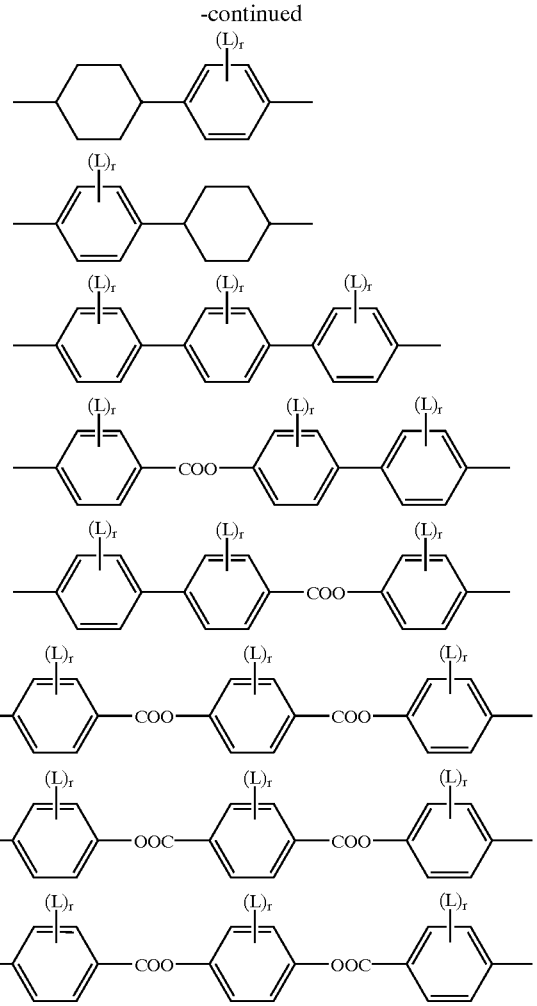

wherein L has the meaning given above and r is 0, 1 or 2.

The group

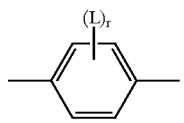

in this preferred formulae is very preferably denoting

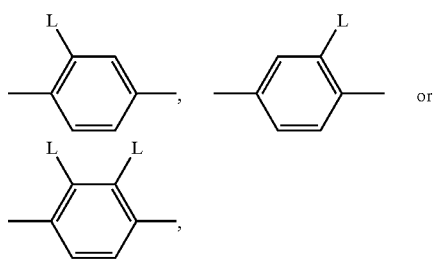

furthermore

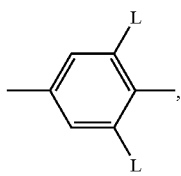

with L having each independently one of the meanings given above.

R in these preferred compounds is particularly preferably CN, F, Cl, OCF$_3$, or an alkyl or alkoxy group with 1 to 12 C atoms or has one of the meanings given for P—(Sp)$_n$—.

If R in formula I is an alkyl or alkoxy radical, i.e. where the terminal CH$_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy, for example.

Oxaalkyl, i.e. where one CH$_2$ group is replaced by —O—, is preferably straight-chain 2-oxapropyl(=methoxymethyl), 2-(=ethoxymethyl) or 3-oxabutyl(=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In the polymerizable mesogenic compounds of formula II R may be an achiral or a chiral group. In case of a chiral group it is preferably selected according to the following formula IV:

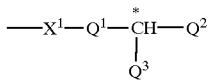
IV wherein
X$^1$ is —O—, —S—, —CO—, —COO—, —OCO—, —OCOO— or a single bond, Q$^1$ is an alkylene or alkylene-oxy group with 1 to 10 C atoms or a single bond, Q$^2$ is an alkyl or alkoxy group with 1 to 10 C atoms which may be unsubstituted, mono- or polysubstituted by halogen or CN, it being also possible for one or more non-adjacent CH$_2$ groups to be replaced, in each case independently from one another, by —C≡C—, —O—, —S—, —NH—, —N(CH$_3$)—, —CO—, —COO—, —OCO—, —OCO—O—, —S—CO— or —CO—S— in such a manner that oxygen atoms are not linked directly to one another, or alternatively has the meaning given for P—Sp—, Q$^3$ is halogen, a cyano group or an alkyl or alkoxy group with 1 to 4 C atoms different from Q$^2$.

Preferred chiral groups R are 2-butyl(=1-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, for example.

In addition, mesogenic compounds of the formula II containing an achiral branched group R may occasionally be of importance as comonomers, for example, due to a reduction in the tendency towards crystallization. Branched groups of this type generally do not contain more than one chain branch. Preferred achiral branched groups are isopropyl, isobutyl(=methylpropyl), isopentyl (=3-methylbutyl), isopropoxy, 2-methylpropoxy and 3-methylbutoxy.

In another preferred embodiment R in formula II is denoting a chiral group that is selected from the following groups:

an ethylenglycol derivative

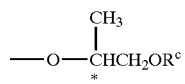

wherein R$^c$ is an alkyl radical with 1 to 12 C atoms, or a group based on citronellol.

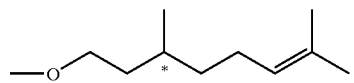

In another preferred embodiment of the present invention the compounds of formula II comprise a mesogenic or mesogenity supporting group MG having at least one center of chirality. In these compounds MG is preferably selected according to formula IIIa:

—(A$^1$—Z$^1$)$_i$—G     IIIa wherein
A$^1$ and Z$^1$ have the meaning given in formula III,
i is 0, 1 or 2,
G is a terminal chiral group, such as for example a cholesteryl group,

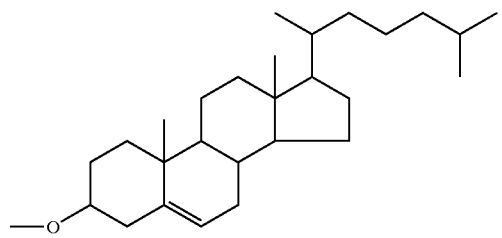

a 2,3-dihydrobenzopyran group

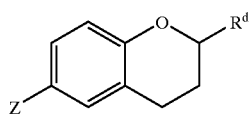

wherein R$^d$ is C$_1$–C$_{12}$ alkyl or alkoxy and Z is —COO— or —O—CO—, or a terpenoid radical like, for example, menthol,

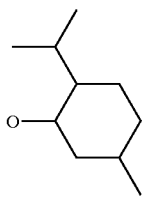

As for the spacer group Sp in formula II all groups can be used that are known for this purpose to the skilled in the art.

Preferably Sp in formula II is a group of the formula S—X, wherein X is the linkage group to the mesogenic group MG and is denoting —O—, —S—, —CO—, —COO—, —OCO—, —OCOO— or a single bond, and S is a linear or branched alkylene group having 1 to 20 C atoms, in particular 1 to 12 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)—, —CH(CN)—, —CH=CH— or —C≡C—.

Typical groups S are for example —$(CH_2)_o$—, —$(CH_2CH_2O)_r$—$CH_2CH_2$—, —$CH_2CH_2$—S—$CH_2CH_2$— or —$CH_2CH_2$—NH—$CH_2CH_2$—, with o being an integer from 2 to 12 and r being an integer from 1 to 3.

Preferred groups S are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyl-iminoethylene and 1-methylalkylene, for example.

In a preferred embodiment of the invention the polymerizable mesogenic compounds of formula II comprise a spacer group of the formula S—X wherein S is a chiral group of the formula V:

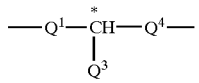

wherein $Q^1$ and $Q^3$ have the meanings given in formula IV, and $Q^4$ is an alkylene or alkylene-oxy group with 1 to 10 C atoms or a single bond, being different from $Q^1$.

In particular preferred are compounds of formula II wherein n is 1.

In the event that R is a group of formula P—Sp—, the spacer groups on each side of the mesogenic core may be identical or different.

In particular preferred are compounds of formula II wherein n is 1.

In another preferred embodiment, the inventive compensator is obtained by copolymerizing mixtures comprising compounds of formula II wherein n is 0 and compounds of formula II wherein n is 1.

In case of chiral compounds the groups Sp and/or MG and/or R are selected such that they contain a chiral C atom, or alternatively chirality is arising from a group inducing molecular asymmetry, such as e.g. a binaphthalene group with restricted rotation.

Typical examples representing chiral and achiral polymerizable mesogenic compounds of the formula I can be found in WO 93/22397; EP 0,261,712; DE 195,04,224; DE 4,408,171 or DE 4,405,316. The compounds disclosed in these documents, however are to be regarded merely as examples that should not limit the scope of this invention.

Furthermore, typical examples representing achiral and chiral polymerizable mesogenic compounds are shown in the following list of compounds, which is, however, to be understood only as illustrative without limiting the scope of the present invention:

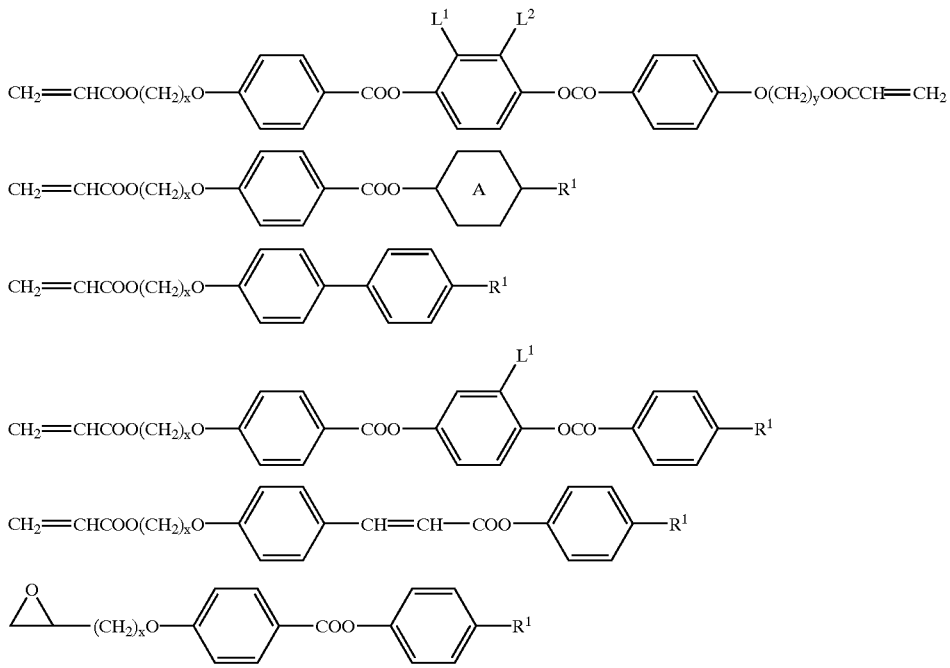

-continued

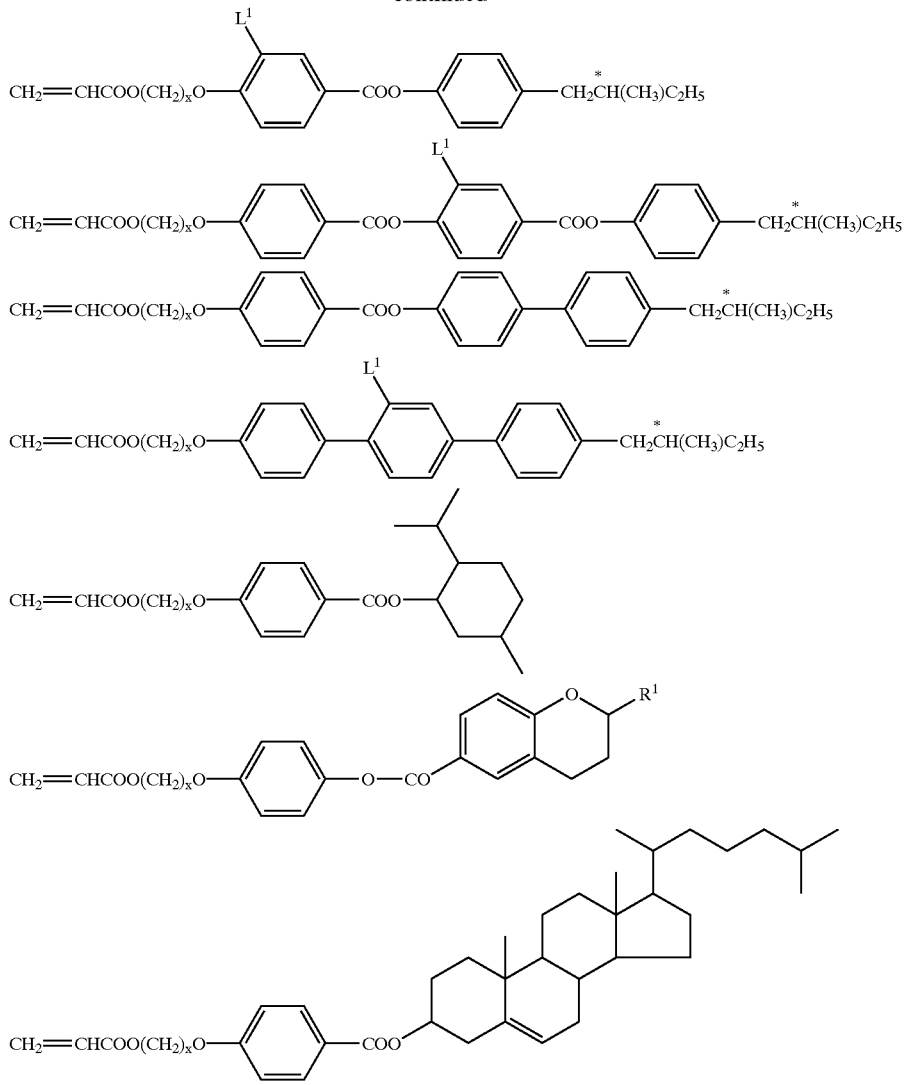

In these compounds x and y are each independently 1 to 12, A is a 1,4-phenylene or 1,4-cyclohexylene group, $R^1$ is halogen, cyano or an optionally halogenated alkyl or alkoxy group with 1 to 12 C atoms and $L^1$ and $L^2$ are each independently H, F, Cl, CN, or an optionally halogenated alkyl, alkoxy or alkanoyl group with 1 to 7 C atoms.

The reactive mesogenic compounds disclosed in the foregoing and the following can be prepared by methods which are known per se and which are described in the documents cited above and, for example, in standard works of organic chemistry such as, for example, Houben-Weyl, Methoden der organischen Chemie, Thieme-Verlag, Stuttgart. Furthermore, detailed methods of preparation can be found for example in D. J. Broer et al., Makromol. Chem. 190, 2255 (1989) or in the patent applications WO 22/3397 or DE 195,04,224.

To induce the cholesteric phase behavior in the chiral polymerizable mesogenic material, for example a mixture comprising an achiral nematic and a chiral nematic polymerizable compound can be used. The chiral nematic compound brings about the helically twisted cholesteric phase structure. Since the pitch of the cholesteric helix is depending on the chemical constitution and the concentration of the chiral compound, the wavelength of the reflection maximum and therewith the color properties of the flakes can be controlled directly in the production process just by varying the type and the ratio of the chiral mesogenic compound. Thus tailor-made pigment flakes with the desired colors can be prepared.

Besides the above mentioned components, the mixture may comprise one or more other suitable components such as, for example, catalysts, light- or temperature-sensitive initiators, stabilizers, co-reacting monomers or surface-active compounds. It is alternatively possible to add, for example, a quantity of up to 20% by weight of a nonpolymerizable liquid-crystalline material to adapt the optical properties of the product. It is also possible to add up to 20% of a non mesogenic compound with one or more polymerizable functional groups to increase crosslinking.

In a preferred embodiment of the present invention, the chiral polymerizable mesogenic material comprises the following components A2) an achiral polymerizable mesogenic compound having two polymerizable functional groups, B) a chiral polymerizable mesogenic compound having one polymerizable functional group, C) a photoinitiator.

D) optionally a non-mesogenic polymerizable compound having two or more polymerizable functional groups, Particularly preferred is a chiral polymerizable mesogenic material according to this preferred embodiment, comprising a) 10–85%, preferably 20–75% by weight of component A2, b) 10–90%, preferably 15–85% by weight of component B, c) 0.01–5%, preferably 0.02–3% by weight of component C, d) 0–20%, preferably 1–15% by weight of component D.

In another preferred embodiment, the chiral polymerizable mesogenic material comprises the following components A1) at least one achiral polymerizable mesogenic compound having one polymerizable functional group, A2) an achiral polymerizable mesogenic compound having two polymerizable functional groups, B) a chiral polymerizable mesogenic compound having one polymerizable functional group, C) a photoinitiator.

Particularly preferred is a chiral polymerizable mesogenic material according to this preferred embodiment, wherein component A1 comprises one to six, preferably one to three achiral polymerizable mesogenic compounds having one polymerizable functional group.

Further preferred is a chiral polymerizable mesogenic material according to this preferred embodiment, comprising a1) 15–85%, preferably 20–75% by weight of component A1, a2) 5–80%, preferably 10–65% by weight of component A2, b) 5–80%, preferably 15–70% by weight of component B.

c) 0.01–5%, preferably 0.02–3% by weight of component C.

Further preferred are chiral polymerizable mesogenic materials comprising the components A1 and C, and optionally the components A2, B and D as described above, together with at least one chiral polymerizable mesogenic compound having two polymerizable functional groups, The ability of a chiral compound to induce a cholesteric structure with a helical twist of a certain pitch in a nematic host is called its helical twisting power (HTP). If a material with a high HTP is used, only a small amount is sufficient to achieve reflection of visible light. In this case it is not necessary that the pure chiral compound exhibits a liquid crystal phase. Only in the mixture with the achiral mesogenic compound a liquid crystal phase should be achieved.

The mixture of the achiral and chiral polymerizable mesogenic compounds is coated onto a substrate, aligned and cured into a polymer film. As a substrate for example a polyester (PET) film can be used. To achieve uniform alignment with planar orientation, i.e. orientation of the helix axes normal to the surface of the coated mixture, the film can be sheared for example by means of a doctor's blade. In another preferred embodiment, a second PET layer is laminated on top of the coated material. In this case, the shearing caused by putting the two substrates together is sufficient to give good alignment.

The alignment is carried out in the cholesteric phase of the mixture of the mesogenic compounds prior to polymerization. Therefore alignment of a high quality can be achieved considerably easier than for a coated polymer film as described in prior art due to the lower viscosity of the unpolymerized material. The application of electric or magnetic fields is not necessary.

Furthermore, since mixtures of polymerizable mesogenic monomers normally exhibit broad nematic or cholesteric mesophase ranges with relatively low melting temperatures, the film can be aligned and cured at temperatures below 100° C., preferably between 30 and 80° C.

Due to the temperature dependency of the cholesteric pitch the variation of the curing temperature leads to flakes with different reflection maxima and is therefore another way to control the color properties of the flakes, in addition to variation of the ratio of the chiral and achiral polymerizable mesogenic compounds.

In the curing process the polymerizable groups of the aligned material react to form a crosslinked polymer film. With propagating polymerization the material becomes glassy and the helical orientation is frozen in. The polymerization can be carried out for example by exposure to UV light with the help of a photoinitiator that decomposes under irradiation to produce free radicals that start the polymerization reaction. In another preferred embodiment a cationic photoinitiator is used that photocures with cations instead of free radicals. The polymerization may also be started by an initiator that decomposes when heated above a certain temperature.

To exclude oxygen that may inhibit the free radical polymerization, a second PET layer may be laminated on top of the coated material, or alternatively the curing can be carried out under a nitrogen atmosphere. In the latter case shearing of the mesogenic material prior to polymerization is necessary to cause sufficient alignment of the cholesteric phase. When using a cationic photoinitator oxygen exclusion is not needed, but water should be excluded.

These methods, however are only to be understood as examples that should not limit the scope of the invention. The person skilled in the art can easily find other suitable ways to carry out the polymerization.

Since the mixture may contain both polymerizable components with one (monofunctional) and with two or more polymerizable groups (multifunctional), polymerization and crosslinking are carried out in the same process. This is in contrast to prior art that describes the use of cholesteric LC polymers that may optionally be crosslinked in a separate step or of non-polymerizable low molar mass cholesteric LC's, but gives no hint to the use of multifunctional polymerizable compounds.

By varying the concentration of the multifunctional mesogenic or non mesogenic components the crosslink density and thereby the product properties such as glass transition temperature, which is also important for the temperature dependence of the optical properties, thermal and mechanical stability or solvent resistance can be tuned easily. According to the desired application flexible or brittle films can be made. A higher brittleness is desirable in particular when the polymer film is subsequently ground to small flakes.

A high brittleness can also be achieved by using compounds with more than two polymerizable groups which may be mesogenic or non mesogenic. Typical examples for non mesogenic monomers with more than two polymerizable groups are trimethylpropanetrimethacrylate or pentaerythritoltetraacrylate.

Flakes can be formed by grinding the cured polymer film, for example by means of a pestle and mortar or by using a mechanized grinder or mill. By additional cooling to temperatures below 0° C. the polymer brittleness is increased and grinding is made easier. The resulting powder is then sieved to give pigment flakes of the desired size.

A preferred method to produce flakes of spherical shape with dimensions smaller than 100 μm is grinding with a pestle and mortar by hand or in a mechanized mortar mill.

Another method to produce more or less spherical flakes is by milling the polymer film in a ball mill. Depending on the size and the weight of the balls, particles with average dimensions of less than 100 μm, in particular of 5 to 10 μm can be obtained.

Another preferred method is milling the polymer film under cooling in a blade mill. This produces a powder of platelet shaped flakes with lateral dimensions from several hundreds of microns to 1 to 2 mm. These flakes can subsequently be ground further in a mortar to give platelets with lateral dimensions smaller than 100 μm.

Cooling of the sample during grinding or milling can be achieved for example by using a carbon dioxide/acetone bath. Another preferred method of cooling is the addition of dry ice powder or liquid nitrogen to the sample.

In some embodiments it is preferable to add an antistatic agent when milling the polymer material to avoid agglomeration of the particles.

Apart from the method described above, there are further preferred methods to produce chiral polymer flakes according to the invention:

In another preferred embodiment the flakes are made by coating the chiral polymerizable mesogenic material onto a substrate which contains shallow indentations with a diameter of 10 to 100 μm, preferably 20 to 50 μm and a depth of 3 to 20 μm, preferably 4 to 10 μm. In this case the act of coating causes sufficient shear to give uniform alignment. In order to increase the quality of the alignment the material may additionally be sheared for example by means of a doctor's blade or by applying a second substrate on top of the coated material as described above.

In yet another preferred embodiment the chiral polymerizable mesogenic material is gravure printed in the shape of small droplets onto a substrate, for example a polyester web, using a gravure printing plate to leave droplets with a thickness of 3 to 20 μm, preferably 4 to 10 μm and a diameter of 10 to 100 μm, preferably 20 to 50 μm. The act of printing causes sufficient shear to give uniform alignment, however, here also the material may be additionally aligned by shearing with for example a doctor's blade or by appliying a second substrate on top of the droplets.

Another preferred method to produce cholesteric flakes comprises spraying of the chiral polymerizable mesogenic material into an $N_2$ atmosphere to give small droplets with a diameter of 10 to 100 μm, which are cured by irradiation with strong UV light. The cured droplets may subsequently be ground to make smaller flakes.

Another preferred method is to coat the chiral polymerizable mesogenic material onto a rotating drum, align by a knife edge, cure by irradiation with UV light and scrape off the cured polymer to yield small flakes.

In another preferred method the chiral polymerizable mesogenic material is coated onto a rotating drum containing dimples with a depth of 2 to 20 μm, preferably 3 to 10 μm and a diameter of 10 to 100 μm, preferably 20 to 50 μm, cured by UV irradiation and peeled off the drum.

In another preferred method the chiral polymerizable mesogenic material is coated onto a rotating drum containing stripes that are 2 to 20 μm, preferably 3 to 10 μm deep and 10 to 100 μm, preferably 20 to 50 μm across, aligned and cured as described above. After this the stripes are ground into fragments of the desired size.

In another preferred method an emulsion of the chiral polymerizable mesogenic material in an immiscible liquid is made and the droplets are polymerized by heating or UV irradiation.

In another preferred method a surfactant is added to the chiral polymerizable mesogenic material and $N_2$ gas blown in to make a foam which is polymerized, scraped off and ground.

Another preferred method uses a solid particle, preferably carbon black or graphite dipersed in a solution of the chiral polymerizable mesogenic material and two solvents. Solvent 1 does not dissolve the chiral polymerizable mesogenic material but solvent 2 does. Solvent 2 is boiled off and the precipitating chiral polymerizable mesogenic material forms a coating over the carbon particle which is then polymerized. This method produces particularly bright flakes.

In yet another preferred method the chiral polymerizable mesogenic material is extruded under pressure through one or more slots with a width of 2 to 20 μm, preferably 3 to 10 μm, whereby the shearing produces good uniform alignment. The film is cured in an $N_2$ atmosphere.

The flakes obtained by the above mentioned methods have dimensions of several microns. It is also possible, however, to chose the process parameters so that flakes with lateral dimensions of 500 μm to 1.5 mm are obtained. These flakes show particularly striking color effects and are preferred in certain applications.

For the use in inks and paints, the cholesteric pigment flakes can be dispersed in a transparent binder or fluid, or incorporated into plastics, depending on the application.

For some applications, it is preferable to use mixtures of flakes with different reflection maxima.

Applications

The cholesteric polymer flakes can be be used as effect pigments in spraying or printing inks or paints or colored plastics for decorative applications like for example cosmetic products. Other important fields of application are automotive use, active or passive optical elements, like e.g. optical films such as polarizers or compensators, and the security sector, for example in false-proof security labels such as ID cards, credit cards or tickets.

As explained in detail above, a considerable advantage of the invention lies in the fact that the optical and the mechanical properties of the pigment flakes can all be controlled in one and the same process simply by changing the type and the concentration of the chiral and achiral, mono- and multifunctional mesogenic polymerizable compounds. Thus the pigment flakes can be tailored appropiately for the desired application.

The complete disclosure of all applications, patents and publications mentioned hereinbefore and hereinafter is introduced into this application by way of reference.

Without further elaboration, it is believed that one skilled in the art can, using the preceding description, utilize the present invention to ist fullest extent. The following examples are, therefore, to be construed as merely illustrative and not limitative of the remainder of the disclosure in any way whatsoever.

In the foregoing and following examples, all temperatures are set forth uncorrected in degrees Celsius and unless otherwise indicated, all parts and percentages are by weight. The following abbreviations are used to illustrate the liquid crystalline phase behavior of the compounds:

C=crystalline; N=nematic; S=smectic; Ch=cholesteric; I=isotropic. The numbers between these symbols indicate the phase transition temperatures in degree Celsius.

EXAMPLES

Example 1

A mixture is formulated consisting of
50% of compound A
49% of compound B and
1% of the commercially available photoinitiator Irgacure 651 (by Ciba Geigy AG, Basel, Switzerland).

Compound A:

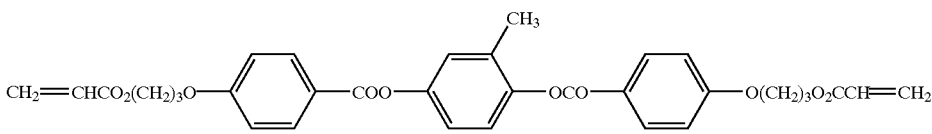

Compound B:

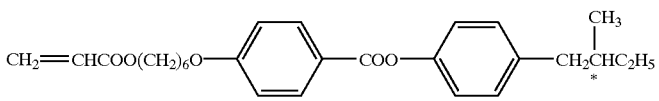

The mixture exhibits the mesophase behavior C 44–47 Ch 53 I and a reflection wavelength of 542 nm at 40° C.

The mixture is coated at 40° C. onto a web of polyester. A second polyester web is laminated over the top to cause alignment of the cholesteric phase and exclude oxygen. The aligned mixture between the two polyester webs is then cured with UV light of a power of 5 mW/cm² to give a green polymer film of 6–8 μm thickness. The polymer film is peeled off the substrates for further processing.

5 g of the polymer film are mixed with 500 g dry ice powder and ground to small flakes using a pestle and mortar. After sieving with a 100 μm sieve, the flakes which passed through the sieve are collected and dispersed into a nitrocellulose binder. The dispersion is sprayed onto a black metal substrate to give a coating that shows a bright iridescent green color at normal incidence and reflects blue light at glancing angles of incidence.

An SEM photograph of pigment flakes of example 1 obtained from a Jeol 6300F electron microscope at an acceleration voltage of 20 kV with a magnification of 1000, shows flakes having globular shape with a diameter ranging from about 3 to about 20 μm.

Example 2

A mixture is formulated consisting of
54% of compound A
45% of compound B and
1% of Irgacure 651
The mixture reflects red light and has the mesophase behavior C 51 Ch 57 i.

The mixture is coated, cured and ground using a pestle and mortar as described in example g to give red polymer flakes with a reflection wavelength of λ=606 nm.

Example 3

A mixture formulated of
47% of compound A
48% of compound B
4% of trimethylpropanetrimethacrylate (as non-mesogenic crosslinking agent) and
1% of Irgacure 651
reflects green light and has a monotropic cholesteric phase when cooled down from the isotropic phase with the mesophase behavior C 41–56 (Ch 36 i).

The mixture is coated, cured and ground using a pestle and mortar as described in example 1 to give green flakes with a reflection wavelength of λ=522 nm.

Example 4

A polymer film produced as described in example 1 is milled in a blade mill from Ika. The resulting powder is mixed with dry ice, ground in a mortar and sieved through a 100 μm sieve. The resulting flakes are dispersed and sprayed on a black substrate as described above to give a coating which shows bright iridescent green color at normal incidence and reflects blue light at glancing angles of incidence.

An SEM photograph of the flakes of example 4 obtained from a Jeol 6300F electron microscope at an acceleration voltage of 5 kV and a distance of 25 mm with a magnification of 100, shows flakes having a platelet shape with a an average thickness of about 10 μm and lateral dimensions of about 100 to 200 μm.

What is claimed is:

1. A cholesteric flake material obtained by polymerizing a chiral polymerizable mesogenic material, having the form of granules of a symmetric or unsymmetric shape.

2. The cholesteric flake material of claim 1, wherein the granules have average dimensions of 1 to 2000 microns.

3. The cholesteric flake material of claim 1, wherein the granules have average dimensions of less than 100 microns.

4. The cholesteric flakes of claim 1, wherein the granules have average dimensions of 5 to 10 microns.

5. The cholesteric flake material of claim 1, having essentially spherical shape.

6. The cholesteric flake material of claim 1, which is obtained by a process including:
   (a) coating a chiral polymerizable mesogenic material onto a substrate which is then optionally covered by a second substrate,
   (b) aligning the coating material into a planar orientation,
   (c) curing The aligned coating material into a crosslinked polymer film,
   (d) removing the crosslinked polymer film from the substrate, and
   (e) grinding it, optionally while cooling, to obtain granules.

7. The cholesteric flake material of claim 1, wherein the chiral polymerizable mesogenic material comprises at least two polymerizable mesogenic compounds exhibiting at least one terminal polymerizable group that is linked, optionally via a spacer group, to a mesogenic core and is selected from the formulae I1–I4;

$$CH_2=CW-COO- \qquad I1$$

$$WCH=CH-O- \qquad I2$$

$$CH_2=CH-Ph-(O)_n- \qquad I3$$

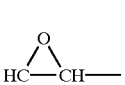 I4 in which W denotes H, $CH_3$ or Cl and n is 0 or 1.

8. The cholesteric flake material of claim 1, wherein the polymerizable mesogenic material comprises at least one achiral polymerizable mesogenic compound and at least one chiral polymerizable mesogenic compound, wherein at least one of these compounds exhibits two or more polymerizable groups.

9. The cholesteric flake material of claim 8, wherein the achiral polymerizable mesogenic compound exhibits two or more polymerizable groups.

10. The cholesteric flake material of claim 8, wherein the chiral polymerizable mesogenic compound exhibits two or more polymerizable groups.

11. The cholesteric flake material of claim 1, wherein the chiral polymerizable mesogenic material comprises at least one photoinitiator.

12. The cholesteric flake material of claim 1, wherein the chiral polymerizable mesogenic material comprises a non-mesogenic compound with one or more polymerizable groups.

13. The cholesteric flake material of claim 1, wherein the chiral polymerizable mesogenic material comprises at least one compound of formula II:

$$P-(Sp)_n-MG-R \qquad II$$

wherein

P is a polymerizable group selected from formulae I1 to I4, $$CH_2=CW-COO- \qquad I1$$

$$WCH=CH-O- \qquad I2$$

$$CH_2=CH-Ph-(O)_n- \qquad I3$$

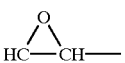 I4 in which W denotes H, $CH_3$ or Cl and n is 0 or 1,

Sp is a spacer group having 1 to 20 C atoms,

R is H, halogen or cyano or a chiral or achiral organic group that may be linear or branched or, in compounds exhibiting more that one polymerizable group, has the meaning given for $P-(Sp)_n-$, n is 0 or 1, and MG is a mesogenic or mesogenity supporting group.

14. The cholesteric flake material of claim 13, wherein MG is a group of formula III:

$$-(A^1-Z^1)_m-A^2-Z^2-A^3- \qquad III$$

wherein $A^1$, $A^2$ and $A^3$ are independently from each other 1,4-phenylene in which, one or more CH groups are optionally replaced by N, 1,4-cyclohexylene in which, one or two non-adjacent $CH_2$ groups are optionally replaced by O and/or S, 1,4cyclohexenylene or naphthalene-2,6-diyl, all of which are unsubstituted, mono- or polysubstituted with halogen, cyano or nitro groups or alkyl, alkoxy or alkanoyl groups having 1 to 7 C atoms wherein one or more H atoms are optionall substituted by F or Cl, $Z^1$ and $Z^2$ are each independently $-COO-$, $-OCO-$, $-CH_2CH_2-$, $-OCH_2-$, $-CH_2O-$, $-CH=CH-$, $C\equiv C-$, $-CH=CH-COO-$, $-OCO-CH=CH-$ or a single bond and m is 0, 1 or 2.

15. The cholesteric flake material of claim 14, wherein MG is selected from the groups of formulae III-1 to III-14

| | |
|---|---|
| —Phe-$Z^2$-Phe— | III-1 |
| —Phe-$Z^2$-CyC— | III-2 |
| —PheL-$Z^2$-Phe— | III-3 |
| —PheL-$Z^2$-Cyc— | III-4 |
| —Phe-$Z^2$-PreL— | III-5 |
| —Phe-$Z^1$-Pne-$Z^2$-Phe— | III-6 |
| —Phe-$Z^1$-Pne-$Z^2$-Cyc— | III-7 |
| —Phe-$Z^1$-Cyc-$Z^2$-Phe— | III-8 |
| —Phe-$Z^1$-Cyc-$Z^2$-Cyc— | III-9 |
| —Phe-$Z^1$-PheL-$Z^2$-Phe— | III-10 |
| —Phe-$Z^1$-Pne-$Z^2$-PheL— | III-11 |
| —PheL-$Z^1$-Phe-$Z^2$-PheL— | III-12 |
| —PheL-$Z^1$-PheL-$Z^2$-Phe— | III-13 |
| —PheL-$Z^1$-PheL-$Z^2$-PheL— | III-14. |

16. The cholesteric flake material of claim 14, wherein MG is selected from the following formulae;

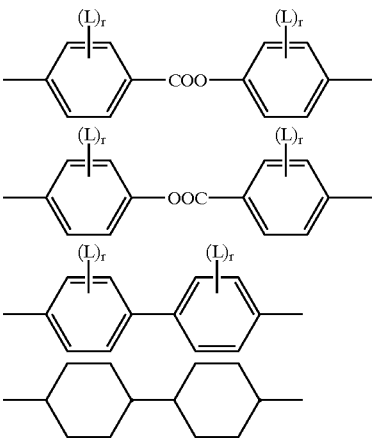

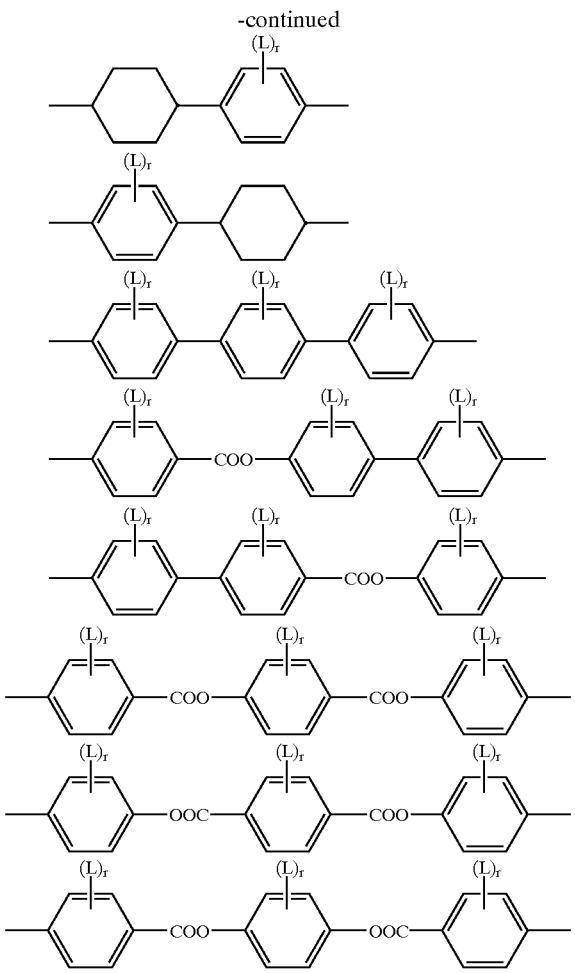

wherein L has the meaning given above and r is 0, 1 or 2.

17. The cholesteric flake material of claim 13, wherein Sp is S—X, with S being linear or branched alkylene with 1–12 C atoms and X being —O—, —S—, —CO—, —COO—, —OCO—, —OCOO— or a single bond.

18. The cholesteric flake material of claim 13, wherein R is P—(Sp)$_n$—.

19. The cholesteric flake material of claim 13, wherein R is CN, F, Cl, OCF$_3$, an alkyl or alkoxy group with 1 to 12 C atoms.

20. The cholesteric flare material of claim 8, wherein the achiral polymerizable compound is a compound of formula II.

21. Cholesteric flakes of claim 1, wherein the chiral polymerizable compound is a compound of formula II:

P—(Sp)$_n$—MG—R     II wherein

P is a polymerizable group selected from formulae I1 to I4,

CH$_2$=CW—COO—     I1

WCH=CH—O—     I2

CH$_2$=CH—Ph—(O)$_n$—     I3

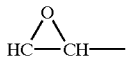 I4 in which W denotes H, CH$_3$ or Cl and n is 0 or 1,

Sp is a spacer group having 1 to 20 C atoms,

R is H, halogen or cyano or a chiral or achiral organic group that may be linear or branched or, in compounds exhibiting more than one polymerizable group, has the meaning given for P—(Sp)$_n$—, n is 0 or 1, and MG is a mesogenic or mesogenity supporting group.

22. The cholesteric flake material of claim 21, wherein R is a chiral group of formula IV:

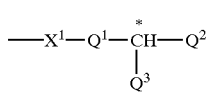 IV wherein

X$^1$ is —O—, —S—, —CO—, —COO—, —OCO—, —OCOO— or a single bond,

Q$^1$ is an alkylene or alkylene-oxy group with 1 to 10 C atoms or a single bond, Q$^2$ is an alkyl or alkoxy group with 1 to 10 C atoms which is unsubstituted, mono- or polysubstituted by halogen or CN, optionally one or more non-adjacent CH$_2$ groups are replaced, in each case independently from one another, by —C≡C—, —O—, —S—, —NH—, —N(CH$_3$)—, —CO—, —COO—, —OCO—, —OCO—O—, —S—CO— or —CO—S—in such a manner that oxygen atoms are not linked directly to one another, or alternatively has the meaning given for P—(Sp)$_n$—, Q$^3$ is halogen, a cyano group or an alkyl or alkoxy group with 1 to 4 C atoms different from Q$^2$.

23. The cholesteric flake material of claim 21, wherein MG is a chiral group of formula IIIa —(A$^1$—Z$^1$)$_l$—G     IIIa wherein A$^1$ is 1,4-phenylene where one or more CH groups are optionally replaced by N and, additionally where one or two non-adjacent CH$_2$ groups are optionally replaced by O and/or S, 1,4-cyclohexenylene; or naphthalene -2, -6diyl; each of these being unsubstituted, mono- or poly-substituted with halogen, cyano or nitro groups or alkyl, alkoxyl or alkanoyl groups having 1 to 7 C atoms, optionally one or more H atoms substituted by F or Cl;

Z$^1$ is —COO—, —OCO—, —CH$_2$CH$_2$—, —OCH$_2$—, —CH$_2$O—, —CH=CH—, —C≡C—, —CH=CH—COO—, —OCO—CH=CH— or a single bond;

l is 0, 1 or 2;

and G is cholesteryl, 2,3-dihydrobenzopyran Dr terpenoid group.

24. The cholesteric flake material of claim 21, wherein Sp is a chiral group of formula V:

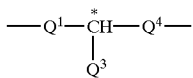

wherein

Q$^1$ and Q$^3$ have the meanings given in formula IV, and

Q$^4$ is an alkylene or aikylene-oxy group With 1 to 10 C atoms or a single bond, being different from Q$^1$.

25. The cholesteric flake material of claim 1, wherein the chiral polymerizable mesogenic materials comprises the components A2, B, C and D
- A2 an achiral polymerizable mesogenic compound having two polymerizable functional groups,
- B a chiral polymerizable mesogenic compound having one polymerizable functional group,
- C a photoinitiator,
- D optionally a non-mesogenic polymerizable compound having two or more polymerizable functional groups.

26. The cholesteric flake material of claim 1, wherein the chiral polymerizable mesogenic materials comprises the components A1, A2, B and C:
- A1 at least one achiral polymerizable mesogenic compound having one polymerizable functional groups,
- A2 an achiral polymerizable mesogenic compound having two polymerizable functional groups,
- B a chiral polymerizable mesogenic compound having one polymerizable functional group,
- C a photoinitator.

27. The cholesteric flake material of claim 1, wherein the chiral polymerizable mesogenic materials comprises the components A1, A2, B, C and D:
- A1 at least one achiral polymerizable mesogenic compound having one polymerizable functional groups,
- A2 an achiral polymerizable mesogenic compound having Two polymerizable functional groups,
- B a chiral polymerizable mesogenic compound having one polymerizable functional group,
- C a photoinitiator,
- D optionally a non-mesogenic polymerizable compound having two or more polymerizable functional groups.

28. A printing ink, spray paint, cosmetic product or colored plastic composition comprising a cholesteric flake maternal of claim 1.

29. An active or passive optical element comprising a cholesteric flake material of claim 1.

30. An ink or paint used for a security application comprising a cholesteric flake material of claim 1.

31. An ink or paint comprising a cholesteric flake material of claim 1 dispersed in a transparent binder or fluid.

32. An automobile ink or paint comprising a cholesteric flake material of claim 1 dispersed in a transparent binder or fluid.

33. An optical film as polarizer or compensator comprising a cholesteric flake material of claim 1.

34. A security label, ID card, credit card or ticker comprising a cholesteric flake material of claim 1.

35. A security label, ID card, credit card or ticket comprising an ink or paint of claim 30.

* * * * *

UNITED STATES PATENT AND TRADEMARK OFFICE
CERTIFICATE OF CORRECTION

PATENT NO. : 6,414,092 B1　　　　　　　　　　　　　　　　　　　　　　　Page 1 of 1
DATED : July 2, 2002
INVENTOR(S) : David Coates et al.

It is certified that error appears in the above-identified patent and that said Letters Patent is hereby corrected as shown below:

Column 18,
Line 59, reads "curing The" should read -- curing the --

Column 20,
Line 12, reads "-CH,CH,-,-OCH," should read -- $CH_2CH_2$-, -$OCH_2$-, --

Column 21,
Line 50, reads "cholesteric flare" should read -- cholesteric flake --

Column 22,
Line 53, reads "-2, -6diyl;" should read -- 2, -6-diyl --
Line 64, reads "Dr terpenoid" should read -- or terpenoid --

Column 23,
Line 9, reads "or aikylene-oxy group With 1" should read -- alkylene-oxy group with 1 --

Column 24,
Line 7, reads "Two" should read -- two --
Line 15, reads "maternal" should read -- material --
Line 27, reads "or ticker" should read -- or ticket --

Signed and Sealed this

Twenty-fifth Day of March, 2003

JAMES E. ROGAN
*Director of the United States Patent and Trademark Office*